(12) United States Patent
Bashkirov

(10) Patent No.: US 7,666,426 B2
(45) Date of Patent: Feb. 23, 2010

(54) METHOD FOR IMMUNE RESPONSE ELICITING IN A MAMMAL

(75) Inventor: Alexey B. Bashkirov, Akademicheskii pr. 12-12, Pushkin, St. Petersburg (RU) 196607

(73) Assignees: Alexey B. Bashkirov, St. Petersburg (RU); Stanislav Leonidovich Kuzmin, St. Petersburg (RU)

( * ) Notice: Subject to any disclaimer, the term of this patent is extended or adjusted under 35 U.S.C. 154(b) by 394 days.

(21) Appl. No.: 11/003,311

(22) Filed: Dec. 3, 2004

(65) Prior Publication Data

US 2005/0152915 A1    Jul. 14, 2005

(30) Foreign Application Priority Data

Jan. 12, 2004   (RU) ............................... 2004101380

(51) Int. Cl.
- A61K 39/00 (2006.01)
- A61K 39/02 (2006.01)
- A61K 39/12 (2006.01)
- A61K 39/38 (2006.01)

(52) U.S. Cl. .............. 424/184.1; 424/204.1; 424/234.1; 424/265.1; 424/277.1

(58) Field of Classification Search .................. 424/93.1
See application file for complete search history.

(56) References Cited

U.S. PATENT DOCUMENTS

| | | | |
|---|---|---|---|
| 4,613,322 A | 9/1986 | Edelson | |
| 4,787,883 A | 11/1988 | Kroyer | |
| 5,571,082 A | 11/1996 | Bashikirov | |
| 6,607,722 B2 | 8/2003 | Edelson et al. | |
| 2001/0053355 A1 | 12/2001 | Edelson | |
| 2002/0004044 A1 | 1/2002 | Edelson | |
| 2002/0098469 A1 | 7/2002 | Edelson | |
| 2002/0114793 A1 | 8/2002 | Edelson | |
| 2003/0187225 A1* | 10/2003 | Penichet et al. ............. 530/351 |
| 2003/0219420 A1 | 11/2003 | Edelson et al. | |

FOREIGN PATENT DOCUMENTS

| RU | 2069573 C1 | 11/1996 |
|---|---|---|
| RU | 2091092 C1 | 9/1997 |

* cited by examiner

*Primary Examiner*—Mark Navarro
(74) *Attorney, Agent, or Firm*—Houston Eliseeva LLP

(57) ABSTRACT

The invention relates to immunology, in particular to methods for influencing the immune system, and may be useful in immunotherapy for diseases of humans and animals, including therapy for oncological, autoimmune, and viral diseases. The invention comprises exposure of tumor cells obtained ex vivo or pathological cells of a non-tumorous nature or of a fraction of a biological fluid of a mammal containing viruses or bacteria to radiation of the optical range in the presence or absence of photochemical agents or treatment of said cells, viruses, or bacteria by other physical factors or chemical substances known in the art. The cells of suspensions containing viruses or bacteria are administered into the lymphatic system of said mammal. Treated cells or suspensions obtained from an exogenous source and possessing their biologically activity before the treatment may also be administered endolymphatically. The method of the invention enhances the efficacy and usability of immunotherapy.

9 Claims, No Drawings

METHOD FOR IMMUNE RESPONSE ELICITING IN A MAMMAL

CROSS-REFERENCE TO RELATED APPLICATION

This application is a continuation of Russian Federation Patent Application No. 2004101380, filed on Jan. 12, 2004, which is hereby incorporated herein by reference in its entirety.

BACKGROUND OF THE INVENTION

The invention relates to immunology, in particular to methods for influencing the immune system, and may be useful in therapy for diseases in mammals (humans and animals), including therapy for cancerous, autoimmune, and viral diseases.

A method for eliciting of an immune response to the formation of tumor cells in mammalian body disclosed in U.S. patent application No. 20030219420 comprises the following:

1) tumor treatment using a conventional method in order to eliminate the bulk of tumor cells in vivo (paragraph 0082 of said application);

2) treatment of a leukocyte concentrate, which is obtained by extracorporeal circulation of the blood of the tumor-bearing mammal, in a way that reduces the amount of blood plasma and serum proteins in the concentrate and, also, initiates the differentiation of monocytes, which, along with other cells, are present in the concentrate, into functional dendritic antigen-presenting cells (referred to hereinafter as APC), said treatment comprising pumping of the leukocyte concentrate through a system of plastic channels and filters; and 3) administering of the treated leukocyte concentrate back into the body.

It is expected that the antigenic structures of the tumor cells upon their interaction with dendritic cells will be presented by the latter, after their administration into the body, to T-cells thus eliciting the immune response of the body.

The basic disadvantage of said method is a high risk of tumor dissemination when it is insufficiently destroyed in vivo, e.g., by photodynamic therapy. Conventional treatments using chemotherapy or tumor irradiation or combinations thereof are known to invariantly compromise the entire immune system of the body. The resulting immunosuppression lasts long enough to make it unreasonable to expect that a significant stimulation of the immune system leading to an immune response will be achieved by administering of differentiated monocytes into the body, even upon the assumption that the monocytes differentiated in that way will have a sufficient functional activity in vivo, which needs sound experimental confirmations obtained in vivo.

Moreover, the author of said Application realizes himself that only a very small amount of the antigenic structures of the cells of a solid tumor may enter the circulatory system after tumor destruction (see paragraph 0053), and so the probability of their contact with the differentiated monocytes administered into the body is also very small. It has been suggested to increase the constant of binding of freely circulating antigenic structures to the treated monocytes administered into the body by additional administering of a certain amount of an antibody, which is specific to a certain type of tumor cells and easily binds to differentiated monocytes. However, it should be noted that, apart from the obvious meshing of treatment technology, the spectrum of antibodies that bind to a certain type of tumor cells is very limited and is far from encompassing all variants possible in the clinical practice.

Another known method for influencing the immune system of a mammal (U.S. Pat. No. 6,607,722; see also U.S. patent applications Nos. 20010053355, 20020098469, 20020114793, and 20020004044) comprises the following:

1) in vitro induction of APC formation from monocytes in a blood sample, which has been withdrawn from the body of the mammal, by a treatment using physical of chemical means;

2) subsequent co-incubation of the monocytes, which have differentiated into APC, with pathological biologically active elements, which have been obtained from the same mammal or are exogenous and which have undergone prior inactivation with physical influences or chemical means; and 3) administering of the mixture so obtained to said mammal.

Pathological biologically active elements (referred to hereinafter as PBE) are to be understood herein as any biological structures capable of causing a pathology and having at least one antigen associated therewith and being an individual immunological marker thereof. The examples of PBE include but are not limited to pathological cells capable of causing a disease (e.g., clones of immunocompetent cells in, e.g., autoimmune diseases), cells infected by a virus or affected by a microorganism, different microbes, viruses, and bacteria that circulate in a body, etc.

The use of the above method affords, according to data provided by its authors, a more prominent therapeutic effect vs. that afforded by the method according to prior art (U.S. Pat. No. 4,613,322), which has been named photopheresis.

At the same time, the method is laborious (see Examples in U.S. Pat. No. 6,607,722) and potentially less efficient than possible alternatives. The artificial in vitro differentiation of monocytes into APC after a prolonged physicochemical influence undermines the expectation that, upon administration of the so obtained APC into the body, their functional activity in vivo will be comparable to the functional activity of APC that have been formed by the natural cell differentiation in the body in the course of the development of an immune response to an antigenic stimulus. The required level of immunoreactivity of the administered immunocompetent cells is ensured by their sufficient amount and so is associated with a large volume of blood to be treated, which is quite traumatic to the patient undergoing such therapy.

The method for administration of the incubated mixture (intravenous, subcutaneous, intradermal, or intramuscular: see disclosure of U.S. Pat. No. 6,607,772) also does not provide for the optimal effect. It is known (see, e.g.: I. Roit, J. Brostoff, D. Male, Immunology, 1998, Mosby International, Ltd.) that the most important for foreign antigens presentation to resting T-cells are not tissue macrophages (including blood monocytes) but rather the so-called interdigital cells (referred to hereinafter as IDC) of the regional lymph nodes. APC located in the skin and other flat epithelium coatings of the body and, also, blood monocytes become transformed into IDC and capable of efficient antigen presentation to T-helpers for eliciting of the systemic immune response only after they have migrated via afferent lymphatics to the paracortical compartments of regional lymph nodes and have interacted with a series of T-cells there. As to the forced-differentiated blood monocytes administered into the body within the total cell mass, they can induce the generalized immune response only subsequent to the transfer of specific PBE markers bound thereto to the regional organs of the peripheral immune system.

Therefore, basing on the above, the method that appears to be the most similar to the method of the present invention is the method disclosed in U.S. Pat. No. 5,571,082 and implying the direct contact of processed antigens with IDC. According to said method, a leukocyte-enriched suspension obtained from a body liquid of a patient is exposed to optical radiation (within the visible of ultraviolet spectral regions) in the presence of a photochemical agent and then is returned back directly into the lymphatic system of the patient undergoing such treatment. When photo-adducts generated as a result of the covalent binding of the molecules of the photochemical agent to the components of pathological antigenic structures (e.g., antigenic structures of clones of pathological immunocompetent cells in lymphoproliferative malignant diseases or autoimmune conditions, of cells affected by viruses or bacteria, of viruses and bacteria circulating in the body, etc.) present in the fraction administered into the lymphatic system arrive in the body, their direct contact with IDC provides for the generalized immune response elicited in vivo without making damage to IDC and to the cells of the peripheral immune system. This does not require a special incubation of blood monocytes with the antigenic structures of pathological cells, viruses, or bacteria.

The main disadvantage of the above method is that the field of its application in the clinical practice is limited to pathological conditions (viral and bacterial infections, autoimmune conditions, and diseases of the blood and lymph systems, including blood and bone marrow malignancies) where the specific antigenic structures targeted by the immune response of the body are present directly in the biological fluids of a patient.

BRIEF SUMMARY OF THE INVENTION

The method of the present invention expands the application field of the lymphophotopheresis method of U.S. Pat. No. 5,571,082 by making it possible to elicit immune response against any tumor cells, including solid tumor cells and, also, to make preventive immunizations against viruses and bacteria.

According to the first aspect of the present invention, the method for immune response eliciting in a mammal comprises obtaining of pathological biologically active elements from the mammal or from an exogenous source, said pathological biologically active elements being the cells of a tumor of any localization or pathological cells of a non-tumorous nature, or viruses or bacteria, transformation of the pathological biologically active elements into a liquid suspension, exposure of the liquid suspension to radiation of the optical range, and administering of said liquid suspension into the lymphatic system of the mammal.

It is preferred that the non-tumorous pathological cells of the mammal are immunocompetent cells affected by a virus or bacteria and showing a pathological reactivity.

It is further preferred that the irradiation of the suspension of the pathological biologically active elements is carried out in the presence of a photochemical agent.

It is still further preferred that the irradiation of the suspension of the pathological biologically active elements is carried out in the presence of a photochemical agent and, also, in the presence of oxygen.

Irradiation of the suspension of the pathological biologically active elements may also be carried out in the presence of oxygen without any photochemical agent.

It is convenient to administer the irradiated suspension of the pathological biologically active elements by means of catheterization or puncture of the lymphatic system of the lower limb body segment.

The suspension of the pathological biologically active elements may be irradiated by exposing thereof to UV impulses or to a constant radiation flow.

According to the second aspect of the present invention, the method for immune response eliciting in a mammal comprises obtaining of a biological fluid from the mammal, obtaining of pathological biologically active elements from the mammal, said pathological biologically active elements being the cells of a tumor of any localization or pathological cells of a non-tumorous nature, or viruses or bacteria, enriching of the biological liquid with pathological biologically active elements, exposure of the biological liquid enriched in the biologically active elements to radiation of the optical range, and administering of the irradiated biological liquid enriched in the biologically active elements into the lymphatic system of the mammal.

It is preferred that the non-tumorous pathological cells of the mammal are immunocompetent cells affected by a virus or bacteria and showing a pathological reactivity.

It is further preferred that the irradiation of the biological liquid enriched in the biologically active elements is carried out in the presence of a photochemical agent.

It is still further preferred that the irradiation of the biological liquid enriched in the biologically active elements is carried out in the presence of a photochemical agent and, also, in the presence of oxygen.

In particular embodiments of the present invention, the irradiation of the biological liquid enriched in the biologically active elements may be carried out in the presence of oxygen without any photochemical agent.

It is preferred that administration of the irradiated biological liquid enriched in the biologically active elements is carried out by means of catheterization or puncture of the lymphatic system of the lower limb body segment.

In particular embodiments of the present invention, the biological liquid enriched in the biologically active elements may be irradiated by exposure to UV impulses or to a constant flow of radiation.

In some embodiments of the present invention, the biological fluid may be blood or its components.

In other embodiments of the present invention, the biological fluid may be lymph or its components.

According to the third aspect of the present invention, the method for immune response eliciting in a mammal comprises obtaining of a biological fluid from the mammal, obtaining of pathological biologically active elements from the mammal of from an exogenous source, said pathological biologically active elements being the cells of a tumor of any localization or pathological cells of a non-tumorous nature, or viruses or bacteria, enrichment of the biological liquid with pathological biologically active elements, exposure of the biological liquid enriched in the pathological biologically active elements to any physical factor other than radiation of the optical range, or to a chemical factor, or to a combination of the factors in a way that inactivates said pathological biologically active elements, and administering of the treated biological liquid into the lymphatic system of the mammal.

It is preferred that the non-tumorous pathological cells of the mammal are immunocompetent cells affected by a virus or bacteria and showing a pathological reactivity.

It is further preferred that the administration of the treated biological liquid enriched in the biologically active elements is carried out by means of catheterization or puncture of the lymphatic system of the lower limb body segment.

In particular embodiments of the present invention, the biological liquid enriched in the biologically active elements may be blood or its components.

In other embodiments of the present invention, the biological fluid enriched in the biologically active elements may be lymph or its components.

According to the forth aspect of the present invention, the method for immune response eliciting in a mammal comprises obtaining of pathological biologically active elements from the mammal or an exogenous source, said pathological biologically active elements being the cells of a tumor of any localization or pathological cells of a non-tumorous nature, or viruses or bacteria, transformation of the pathological biologically active elements into a liquid suspension, exposure of the liquid suspension of the pathological biologically active elements to a physical factor other than radiation of the optical range, or to a chemical factor, or to a combination of the factors in a way that inactivates said pathological biologically active elements, and administering of the treated liquid suspension of the pathological biologically active elements into the lymphatic system of the mammal.

It is preferred that the non-tumorous pathological cells of the mammal are immunocompetent cells affected by a virus or bacteria and showing a pathological reactivity.

It is further preferred that administration of the treated liquid suspension of the pathological biologically active elements is carried out by means of catheterization or puncture of the lymphatic system of the lower limb body segment.

In all of its embodiments, the method of the present invention for immune response eliciting in a mammal is distinguished from prior art by the following:
according the first aspect:
administering of a liquid suspension of pathological biologically active elements, said pathological biologically active elements being the cells of a tumor of any localization or pathological cells of a non-tumorous nature, or viruses or bacteria in to the lymphatic system of a mammal; and
obtaining of the pathological biologically active elements from said mammal or an exogenous source;
according the second aspect:
enrichment of a biological fluid with said pathological biologically active elements, which are the cells of a tumor of any localization or pathological cells of a non-tumorous nature, or viruses or bacteria;
obtaining of the pathological biologically active elements from said mammal or an exogenous source of pathological biologically active elements;
according to the third aspect:
enrichment of a biological fluid with said pathological biologically active elements, which are the cells of a tumor of any localization or pathological cells of a non-tumorous nature, or viruses or bacteria;
obtaining of the pathological biologically active elements from said mammal or an exogenous source of pathological biologically active elements;
exposure of the enriched biological fluid to any physical factor other than radiation of the optical range, or to a chemical factor, or to a combination of the factors performed so as to inactivate said pathological biologically active elements,
according to the forth aspect:
administering of a liquid suspension of pathological biologically active elements, said pathological biologically active elements being the cells of a tumor of any localization or pathological cells of a non-tumorous nature, or viruses or bacteria, into the lymphatic system of a mammal;
obtaining of the pathological biologically active elements from said mammal or an exogenous source of pathological biologically active elements;
exposure of the enriched biological fluid to any physical factor differing from radiation of the optical range or to a chemical factor, or to a combination of the factors performed so as to inactivate said pathological biologically active elements.

In their particular embodiments, the aspects of the present invention are distinguished from the prior art by the following:
pathological body cells of a non-tumorous nature, which are immunocompetent cells affected by viruses or bacteria and showing pathological reactivity;
carrying out of irradiation of a biological fluid enriched in pathological biologically active elements by exposure to ultraviolet radiation applied as impulses or as a constant radiation flow.

DETAILED DESCRIPTION OF THE INVENTION

A part of PBE obtained from a mammal by some ex vivo means (e.g., using invasive techniques in case of solid tumors) is transformed by standard immunological methods into a liquid suspension, the suspension is exposed, in the presence of a photochemical agent, to radiation of the optical range in order to inactivate or alter antigenic structures, and the treated suspension is administered back into the lymphatic system of the mammal. A pronounced immune response is observed upon administering of the treated liquid into the lymphatic system. The possibility of immunogenic photo-adducts contact with certain groups of cells in lymphoid organs is determined by the anatomical position of these cells. Where the immunogenic photo-adducts are administered endolymphatically (or into the adipose tissue around lymph nodes or into lymph nodes, which is technically difficult), they are delivered by lymph into lymph nodes, which drain the respective area, where they interact with the dendritic cells of lymphoid follicles and almost completely pass through regional lymph nodes. This results in a strong generalized immune response. Lymph, unlike circulating blood, lacks components that can shield intact healthy lymphocytes present therein from interactions with the immunogenic photo-adduct, so a direct interaction between intact healthy lymphocytes and immunogenic photo-adducts is possible. As a result of the reaction of intact healthy lymphocytes directed against pathological cells, bacteria, or viruses, a systemic immune response will rapidly develop, only small amounts of immunogenic material (10-20 ml) being required to achieve an expressed therapeutic effect. Therefore, one of the mechanisms of the therapeutic effect of the method of the present invention is, probably, building up of a threshold level of complexes between IDC and T-cell-presented specific antigenic structures of pathological cells in the lymphatic system. The pathological cells as referred to herein are to be understood as cells of tumors of different localizations and cells affected by viruses or bacteria.

The consistence of the suspension may be varied by adding autologous plasma or serum.

Photoactive chemical agents that may be used according to the present invention include but are not limited to active furocoumarins, in particular psoralens and derivatives thereof, porphyrins and protoporphyrins, fluorescein, rhodamine, and complexes of polypeptides with photoactive compounds.

The most widely used in the current art are 8-methoxypsoralen derivatives, which strongly absorb UV radiation within the range of 300 to 400 nm. A therapeutic effect is achievable with any mode of exposure to ultraviolet radiation, either impulses or constant radiation flow.

The therapeutic effect may be enhanced by performing catheterization or puncture within the lower limb body segment because photo-adducts that enter the lymphatic system pass a significantly longer way via lymphatic ducts than in case of catheterization of the upper segments of the lymphatic system.

The method of the present invention does not require a time consuming and laborious co-incubation of monocytes, which have been isolated from the body beforehand, with antigens, which are associated with PBE structures, in order to differentiate monocytes into APC capable of presenting said antigens to T-cells, said procedure being crucial in corresponding methods of other inventions (see paragraph 59 of U.S. patent application No. 20030219420). The process of presentation of specific PBE antigens to T-cells occurs in the natural way in the lymphatic system itself, which makes the process much more efficient.

It is to be understood that in order to elicit in a mammal an immune response against PBE-associated antigens in a manner sparing for said mammal and in order to optimize the development of the immune response, it is preferable to administer treated PBE suspension not at once but gradually over a time ranging from ten minutes to 24 hours and more. This time is determined by the dose of the "autogenous stimulus" and may vary depending on the embodiment of the method of the present invention.

The method of the present invention is easy to use. It makes possible to carry out procedures according to any regimen prescribed by a physician over the whole period of lymphatic duct catheterization.

Before a suspension prepared from tumor cells is administered to a mammal, tests are carried out to determine whether tumor cells have been treated to a sufficient extent (e.g., using vital stains). In case of viruses or bacteria, their inactivation is assesses using appropriate tests.

Treatment of PBE that have specific antigenic markers is required for complete PBE inactivation in order to exclude the possibility of the secondary infection of a mammal receiving therapy according to the present invention. At the same time, the intensity of the treatment must be such as to spare a portion of specific PBE-associated antigens.

Treatment mode is not limited to irradiation of PBE fractions in the presence of a photochemical agent. PBE destruction incompatible with their functionality and ability to proliferate yet associated with an alteration of their antigenic determinants may be also achieved by irradiation of said PBE fractions with ultraviolet light without using photochemical agents (see Union of Soviet Socialist Republics Patent No. 1802922), by thermal treatment (see U.S. Pat. No. 4,787,883), by treatment with chemical substances, by biochemical treatment known in the art (enzymatic destruction of biological structures), etc.

Where ultraviolet radiation is used to treat PBE fractions (irrespective of the presence of a photochemical agent), it is preferable to carry out irradiation in the presence of oxygen as disclosed in Russian Federation Patent Nos. 2069573 and 2091092.

To elicit in a mammal the generalized immune response according to the present invention, it is possible not only to treat PBE-associated antigens obtained ex vivo, but also to treat suspensions of exogenous cultures of PBE using physical or chemical techniques and then to administer such suspension to the mammal endolymphatically and thus to achieve a sort of "vaccination" of the mammal.

Examples of some embodiments of the method of the present invention as realized in a series of preliminary experiments are presented below. The experiments were carried out using cattle of the black-spotted stock breaded at Tosnenskiy Stock Farm of Leningradskaya Oblast, Russian Federation.

EXAMPLE 1

Object: a bull aged 1.5 years.

Diagnosis: extensive preputial fibropapillomatosis (fibrous connective tissue papillomas)

A part of papillomas amounting to about 1 g was removed by surgery.

The bull did not receive the conventional therapy comprising 3 to 5 intravenous injections of 50 to 80 ml of 1% Novocaine over intervals lasting for 4 to 5 days.

About 100 ml of whole blood was withdrawn from the jugular vein of the bull. The bulk of blood plasma was removed by centrifugation, and the remaining blood cells were infused back to the bull.

The excised pathological tissue was homogenized using a standard homogenizer.

The homogenate was added with 10 ml of autologous plasma and 10 ml of saline. After vigorous stirring, the resulting suspension was centrifuged and the supernatant was discarded. This washing procedure was repeated twice.

After the second washing, the resulting preparation of pathological cells was added with 10 ml of autologous plasma and 10 ml of saline. The resulting mixture was exposed to ultraviolet radiation without using a photochemical agent in a chamber ensuring the presence of free oxygen during irradiation (see Russian Federation Patent 2038105), the source of the radiation being OSM-1 apparatus (Lumex, Saint-Petersburg, Russia) having emittance maximum at 254 nm. The rate of irradiation at the surface of the irradiated mixture was 2.3 $W/cm^2$.

The irradiated suspension was infused over 2-4 h into the lymphatic system by performing inguinal lymph duct puncture. During the procedure, the bull was fixed in the cattle-pen as it is conventional in veterinary practice.

The whole procedure was repeated after 7 days. As soon as 2-3 days after the first procedure, most of papillomas shrank and some of them disappeared. By the 12th day of the treatment, all papillomas disappeared.

EXAMPLE 2

Object 1: a cow aged 2,5 years.

Object 2: a cow aged 2 years.

Diagnosis: Viral B-cell leukemia. The total volume of blood leukocytes exceeds the norm more than 2.5 times.

Diagnostics: Serological diagnostics was carried out using standard agar immunodiffusion (AID) blood test kits.

Using a 250-mk syringe, 250 ml of blood was withdrawn from the jugular vein of Object 1 serving as a donor whose blood was immunologically compatible with blood of Object 2. Blood was withdrawn thrice to make its total volume 750 ml. Leukocytes were obtained from the withdrawn blood by centrifugation.

From the jugular vein of Object 2, 50 ml of blood was obtained. The blood sample was centrifuged, plasma was collected, and the residue was administered back to the jugular vein.

The suspension of leukocytes obtained from Object 1 was diluted with blood plasma obtained from Object 2 and added with a solution of industrial grade 8-methoxypsoralen (Oxoralen) to make 1 mg of the photochemical agent per 1 ml of the resulting suspension.

The suspension having Oxoralen dissolved in it was irradiated in a "there-and-back" flow mode at a 1-ml/min flow rate in the presence of oxygen. The source of radiation was Q-139 lamp (Hungary) having a 365-nm emittance maximum. Radiation rate at the surface of the irradiated suspension was 2.5 mW/cm$^2$. The irradiated suspension was administered into the inguinal vein over a 150-minutes period using a medical dropper.

The whole procedure was repeated every fifth day.

After 4 procedures, the treated caw (Object 2) showed a significant improvement of its condition. The results of AID tests turned from "positive" and "non-specific reaction" at the first stage of the treatment into "negative" at the end of the treatment as filed in the Registry of Veterinary Tests of the Tosnenskiy Stock Farm.

The result obtained warrants thorough study and further experimentation to achieve statistical significance. Further optimization of the technique is required for its industrial propagation.

What is claimed is:

1. A method for eliciting immune response in a mammal comprising:
   obtaining non-immunocompetent pathological biologically active elements from the mammal or from an exogenous source;
   transforming the non-immunocompetent pathological biologically active elements into a liquid suspension, wherein the non-immunocompetent pathological biologically active elements prevail as the cellular constituents;
   exposing the liquid suspension to ultraviolet (UV) radiation; and
   administering the liquid suspension into a lymphatic system of the mammal.

2. The method according to claim 1, wherein the exposing of the suspension to the radiation is carried out in presence of oxygen.

3. The method according to claim 1, wherein the administering of the suspension exposed to the radiation comprises catheterization or puncture of a lymphatic system within a lower limb body segment of the mammal.

4. The method according to claim 1, wherein the suspension is exposed to the radiation applied as impulses or as a constant radiation flow.

5. The method according to claim 1, wherein the exposing of the suspension to the radiation is carried out in presence of a photochemical agent.

6. The method according to claim 5, wherein the exposing of the suspension to the radiation is carried out in presence of oxygen.

7. The method according to claim 5, wherein the administering of the suspension exposed to the radiation comprises catheterization or puncture of a lymphatic system within a lower limb body segment of the mammal.

8. The method according to claim 5, wherein the suspension is exposed to the radiation applied as impulses or as a constant radiation flow.

9. The method according to claim 1, wherein the non-immunocompetent pathological biologically active elements comprise non-immunocompetent cells of a tumor of any localization, non-immunocompetent non-tumorous pathological cells, viruses, or bacteria.

* * * * *